US005214455A

United States Patent [19]
Penney et al.

[11] Patent Number: 5,214,455
[45] Date of Patent: May 25, 1993

[54] OBJECTIVE EYE ALIGNMENT MEASUREMENT METHOD AND SYSTEM

[75] Inventors: Carl M. Penney, Saratoga Springs, N.Y.; Keith P. Thompson, Atlanta, Ga.; Robert H. Webb, Lincoln, Mass.

[73] Assignee: General Electric Company, Schenectady, N.Y.

[21] Appl. No.: 677,902

[22] Filed: Apr. 1, 1991

[51] Int. Cl.⁵ .............................................. A61B 3/14
[52] U.S. Cl. ........................................ 351/210; 351/208; 351/246; 356/153
[58] Field of Search ............... 351/210, 208, 206, 246; 356/153

[56] References Cited

U.S. PATENT DOCUMENTS

| 4,213,678 | 7/1980 | Pomerantzeff et al. | 351/210 |
| 4,253,743 | 3/1981 | Matsumura | 351/206 |
| 4,867,554 | 9/1989 | Matsumura | 351/206 |

Primary Examiner—Rodney B. Bovernick
Assistant Examiner—Hung Xuan Dang
Attorney, Agent, or Firm—Paul R. Webb, II

[57] ABSTRACT

Eye alignment is determined by producing a combined iris/retinal image by use of an imaging system. The relative position of the centroid of the pupil and various structures on the retina is indicative of the eye alignment. The eye alignment may be determined by comparing a combined iris/retinal image at the present time with a stored iris/retinal image at a past time. The imaging system may be a laser scanning ophthalmoscope.

22 Claims, 5 Drawing Sheets

OBJECTIVE EYE ALIGNMENT MEASUREMENT METHOD AND SYSTEM

CROSS REFERENCE TO RELATED APPLICATION

This application relates to copending application Ser. No. 557,263, filed Jul. 24, 1990, assigned to the same assignee as the present invention.

BACKGROUND OF THE INVENTION

This invention relates to a system and method for aligning the eyes of a subject.

There are a number of situations where the alignment of a subject's eyes are important. The subject may be human or may be a research animal.

When taking certain types of eye measurements, one may need to know that the eye alignment is in a particular reference position. For example, if one measures the cornea of a person's eye before some type of treatment and one wishes to repeat those measurements after the treatment to determine how much, if any, the treatment has affected the measurements, one must ensure that the eye alignment is in the same position each time the particular measurements are made. Otherwise, the difference in data from before and after the treatment might be due to a change in eye alignment rather than the treatment.

In addition to those situations where one needs to ensure that eye alignment is in the same position for two or more different measurements, there are situations where eye alignment is desirable for diagnostic measurements of eye performance. There are situations when a human subject can simply be requested to fixate on a particular object. Thus, the human may state that he is currently looking at a light source, thereby providing "subjective" eye alignment information. However, there are situations where a doctor or researcher would like "objective" eye alignment information indicating the orientation of the eye and, to the extent possible, indicating what the eye is viewing. For example, very young children cannot be relied upon to fixate on such an object for measurements, such as refraction measurements which are very desirable to ensure that "in focus" images are being received when the child's brain is learning to interpret images. Likewise, adults subjected to extended eye examinations may become tired or subject to other duress and fail to maintain reliable fixation. A patient who is subjected to a therapeutic process such as laser ablation eye surgery may not be able to maintain desired eye orientation over an extended treatment time because of applied anesthesia, fatigue, or distraction by the procedure. Further, a research animal usually cannot be trained to fixate during eye measurements.

In each of the above cases, the failure or inability of the subject to maintain eye fixation upon an object can produce eye measurements or treatments that are seriously in error.

Therefore, there are situations where absolute eye alignment data is needed (i.e., the eye is aligned in a certain manner) and situations where comparative eye alignment data (i.e., the eye is in the same alignment as when earlier measurements were taken) are needed and one cannot rely upon a subject maintaining the alignment.

The use of various optical/electronic systems for making eye measurements has become more common in recent years. One example of such a system is shown in U.S. Pat. No. 4,213,678 to Pomerantzeff and Webb issued on Jul. 22, 1980. That patent discloses a scanning laser ophthalmoscope (SLO) for scanning a portion of the eye fundus. That patent, coinvented by one of the present inventors, is hereby incorporated by reference.

OBJECTS AND SUMMARY OF THE INVENTION

Accordingly, a primary object of the present invention is to provide a new and improved method and system for determining objective eye alignment.

A more specific object of the present invention is to provide objective eye alignment information which may provide the eye alignment relative to some external point or line, such as an instrument axis, or to provide eye alignment information by indicating when the present eye alignment is the same as an earlier eye alignment.

A further object of the present invention is to provide eye alignment data which can be used in combination with other diagnostic and therapeutic instruments. In other words, an object is to allow eye alignment data to be provided without requiring instrumentation which would block or prevent use of diagnostic and/or therapeutic devices which may advantageously use eye alignment information for improving their diagnostic and/or therapeutic operations.

Yet another object of the present invention is to allow one to bring the eye of a subject to a particular desired alignment, while the subject is under general anesthesia or is otherwise unable to cooperate in bringing his eye to a particular alignment.

A still further object of the present invention is to provide eye alignment information in a reliable and convenient fashion.

A more specific object of the present invention is to provide an imaging system and a method of use of an imaging system for determining objective eye alignment.

The above and other objects of the present invention, which will become more apparent as the following detailed description is considered, are realized by a method of determining objective eye alignment. A subject's eye is positioned relative to an imaging system to allow imaging of the eye. The imaging system provides an iris image of an iris portion of the subject's eye and a retinal image of a retinal portion of the subject's eye. The iris image and the retinal image are used to determine objective eye alignment. Preferably, the imaging system obtains the iris image and the retinal image within a time no greater than 50 milliseconds. To minimize intervening eye movements the time of obtaining the images would preferably be substantially less than that. The iris image and the retinal image are simultaneously displayed on a first monitor of the imaging system. (As used herein, "simultaneous display" means that the images appear simultaneous to a human eye.)

The eye alignment may be determined in two different manners. A first way of determining the eye alignment includes the step of comparing the iris image and the retinal image with a stored image of the iris portion and the retinal portion, the stored image corresponding to eye alignment at a previous time. More specifically, this first manner involves finding an eye position at which the iris image and the retinal image are substantially identical to the stored image. A second manner of determining eye alignment involves finding a relationship between an instrument axis of the imaging system and an axis of the subject's eye. More specifically, the axis of the subject's eye may be the pupillary axis.

The iris image and the retinal image are provided by the imaging system scanning a beam across the eye and detecting scatter from the application of the beam to the eye. The beam is preferably a beam of electromagnetic radiation in the infra-red, visible or ultraviolet portions of the spectrum..

The method of the present invention may alternately be described as a method of determining objective eye alignment including a step of scanning a light beam from an imaging system across a subject's eyes such that the light beam strikes an iris portion adjacent a pupil and strikes a retinal portion. Scattered light from the application of the light beam to the iris portion and the retinal portion is then detected by operation of the imaging system. Nearly simultaneous (meaning simultaneous or within 50 milliseconds thereof) views of the iris portion and the retinal portion are generated by operation of the imaging system. The nearly simultaneous views are then used to determine objective eye alignment. The light beam is scanned between extremes of scan which cross in front of the object's eye. More specifically, the extremes of scan preferably cross at least three centimeters in front of the subject's eye (i.e., the closest point on the subject's eye to the scan crossing point is 3 centimeters or greater). The light beam applied to the subject's eye has a diameter of no more than 1 millimeter at the iris.

The system of the present invention is a system for measuring objective eye alignment including a scanner for scanning a beam across a subject's eye such that the beam strikes an iris portion adjacent a pupil and strikes a retinal portion. A detector for detecting scatter from the application of the beam to the iris portion and the retinal portion is operatively connected to a first monitor for showing simultaneous views (i.e., they appear simultaneous to a human eye) of the iris portion and the retinal portion based upon the scatter detected by the detector. The simultaneous views provide objective eye alignment information. More specifically, the scanner scans a light beam. The system may further include a second monitor and storage means to supply the second monitor with a stored image of the iris portion and the retinal portion at a previous time.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
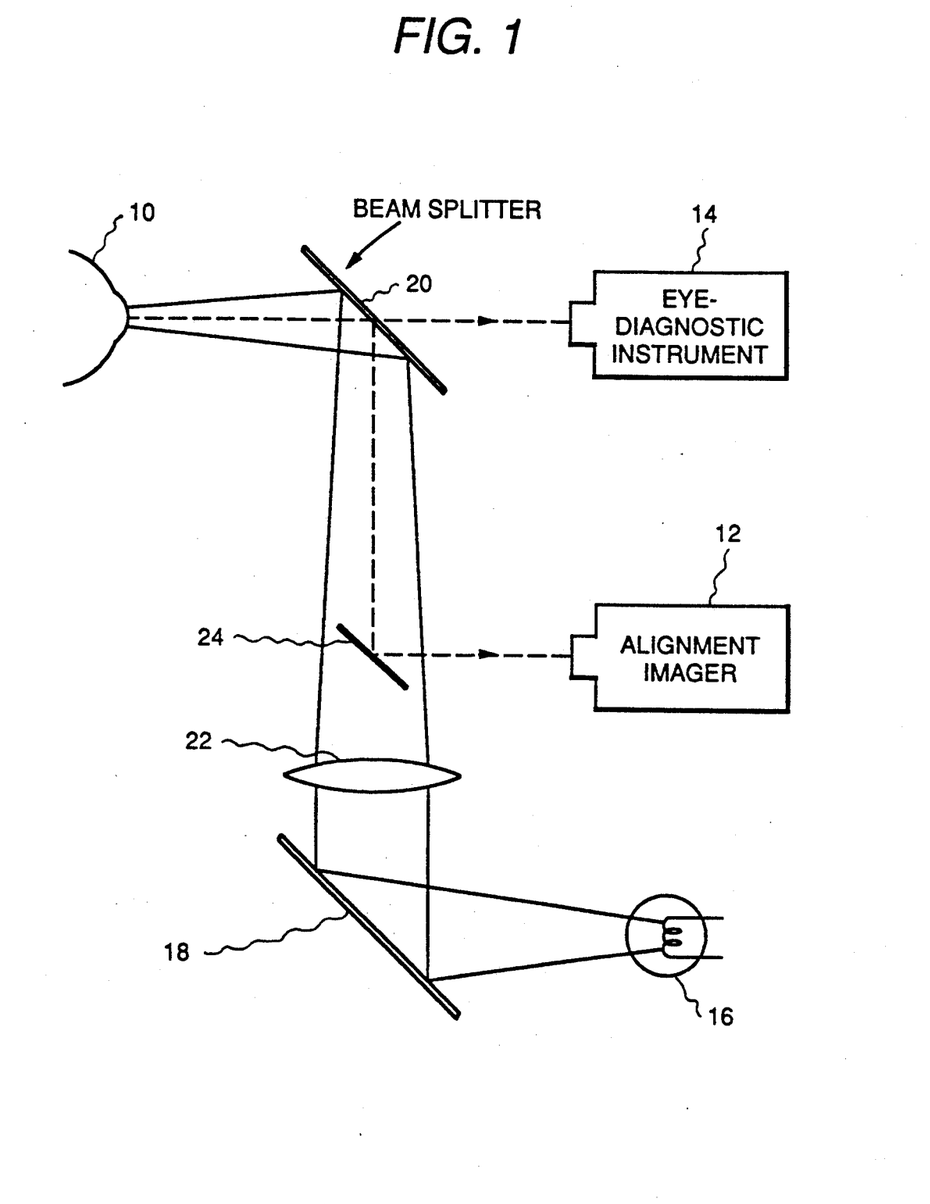
FIG. 1 shows a general schematic diagram illustrating how the present eye alignment system may be used in conjunction with another eye diagnostic instrument.

With reference now to FIG. 1, there is shown a simplified view of part of a subject's eye 10 with an alignment imaging system 12 positioned to allow determination of the eye 10. The alignment imaging system or imager 12 according to the present invention is used to provide eye alignment information in a manner discussed in more detail below. For purposes of an initial general explanation, the arrangement of FIG. 1 shows how this alignment imaging system 12 may be used in combination with some other previously known eye diagnostic instrument 14. In particular, the instrument 14 might be some instrument which may diagnose conditions in the eye 10. The instrument 14 may alternately be some sort of therapeutic instrument (not separately indicated in the diagram) which may be used at the same time as the eye alignment imaging system 12. At any rate, the instrument 14 might be useful independently of any alignment information provided by the alignment system 12 or, more likely, the instrument 14 may use the alignment information from alignment system 12 for more accurately diagnosing and/or applying treatment to the eye 10.

As shown in FIG. 1, a light source 16 may supply light to a reflector 18 which in turn supplies the light to a beam splitter 20 by way of a lens 22. The light from source 16 is applied to the eye 10 and reflects back through the beam splitter 20 to the instrument 14. The eye diagnostic instrument 14 may produce data about the eye 10 depending upon the light reaching the diagnostic instrument 14.

At the same time as the instrument 14 is operating to provide the diagnostic information, the alignment imager 12 uses a reflector 24 and the beam splitter 20 to obtain alignment data about the eye. A manner in which the alignment imager 12 and eye diagnostic instrument 14 may be operated at the same time without one instrument blocking the other is shown in FIG. 1, it being readily appreciated that various other optical configurations could be used. A technique by which light from the alignment imager 12 and light from source 16 used with the instrument 14 can be used at the same time without interfering with each other will be discussed in more detail below, it simply being noted at present that these lights may be at different wavelengths (i.e., different colors) to avoid such interference. It should also be noted that, although the preferred embodiment of the present invention does use an alignment imaging system having a scanned light beam, other imaging systems might possibly be used. Further, the instrument 14 does not necessarily have to be an eye diagnostic instrument using a light source such as source 16. Finally, although FIG. 1 shows the alignment imaging system 12 being used in conjunction with the instrument 14, the alignment imaging system 12 may be used without regard to any other instrument such as instrument 14.

Figure 2:
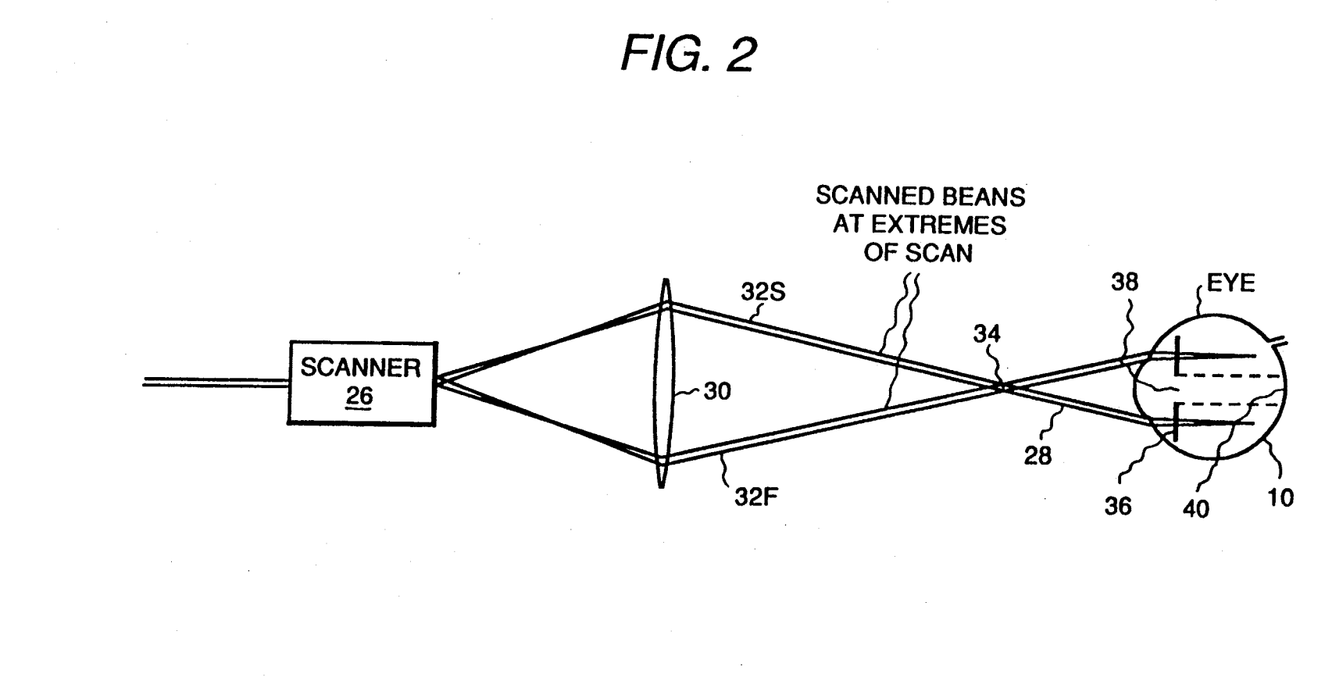
FIG. 2 shows a simplified view illustrating how the present alignment system may apply beams to the eye of a subject.

The manner in which the alignment imager 12 functions to determine the alignment of the eye will be explained by reference to the simplified concept drawing of FIG. 2. As shown in FIG. 2, a scanner 26 scans a beam of light 28 across the eye 10, the beam of light 28 passing through lens 30 prior to its application to the eye 10. As shown, the beam 28 has first and second scan extremes 32F and 32S respectively, which cross at point 34, which point is in front of the subject's eye 10. By crossing in front of the subject's eye, the extremes of scan of beam 28 will allow it to fall upon the edges of iris 36 and, where the beam passes through the pupil 38 within the iris 36, a retinal portion 40 at the back of eye 10. By having the light beam 28 scan across the eye 10 and by using a detector (not shown in FIG. 2, will be discussed in more detail below), the general principle of FIG. 2 may be used to provide a flying spot camera. In order to allow one to have a flying spot camera from the arrangement of FIG. 2 wherein one is able to provide an iris image corresponding to that portion of iris 36 upon which the beam 28 hits and a retinal image corresponding to retinal portion 40, the point 34 at which the extremes of scan cross is typically about 3 centimeters in front of the subject's eye 10 (i.e., the point 34 is about 3 centimeters from the closest point on the eye 10). Additionally, and in order to provide a relatively good focus on the iris portion, the beam 28 will have a beam diameter of no more than 1 millimeter and preferably 0.5 millimeters or slightly above that. In other words, the beam diameter will be at or between 1.0 millimeters and 0.5 millimeters. Note that use of too small a beam diameter would degrade the resolution at the retina 40, whereas use of too large a beam diameter would interfere with the ability of the system to get a good focus on the portions of iris 36 which are around the pupil 38.

In order to fully define the orientation of a generally spherical object such as an eye, certain information is required. If one is using alignment to simply mean the direction of a particular axis of the eye, simply identifying the location of two points along such an axis would indicate the alignment of the eye. However, as used herein, "alignment" will be interpreted as also including information about rotation of the eye about such an axis. Thus, if the particular axis within the eye corresponds to the look direction, rotating the eye about such a look direction axis may maintain the same object in view, even though the orientation of the eye relative to that object has changed. (In practice, the axis within the eye which is used for reference purposes may or may not correspond to the look direction, but this will be discussed in more detail below.) If one wants alignment information to include not only the direction and position of an eye axis but also the rotational position of the eye relative to that axis, this information can be determined by using at least three well-separated points lying in two nearly perpendicular planes. For such a measurement, two of these three points are used to determine the direction and position of the axis, whereas the third point is within a plane normal to the axis, which plane also includes one of the other two points.

Figure 3A:
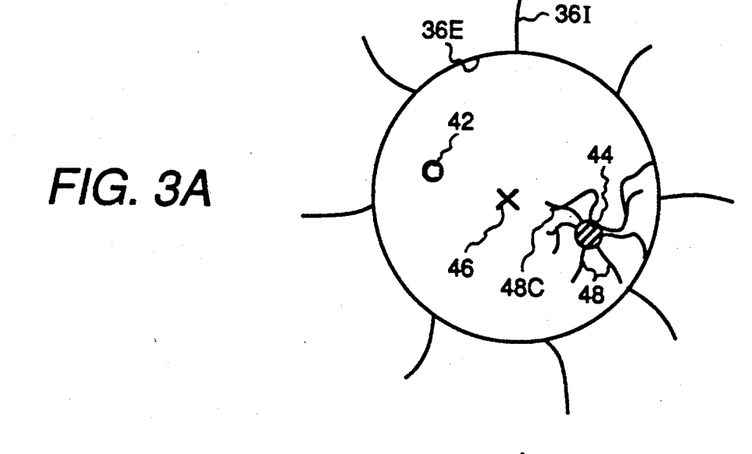
FIG. 3A, 3B, and 3C show separate images which the present system may provide for purposes of determining eye alignment information.
Figure 3B:
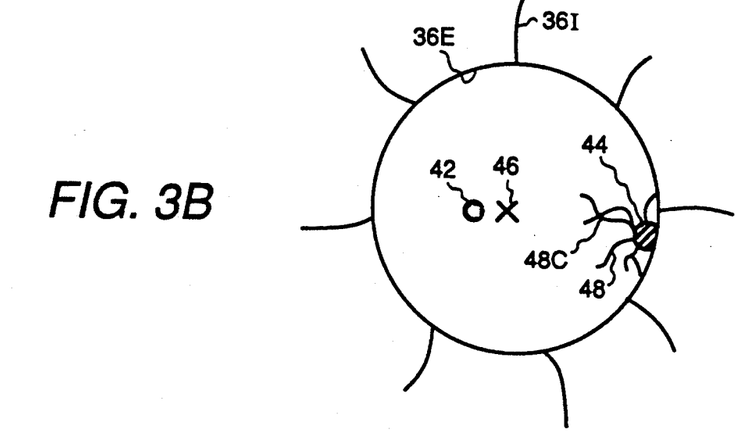
Figure 3C:
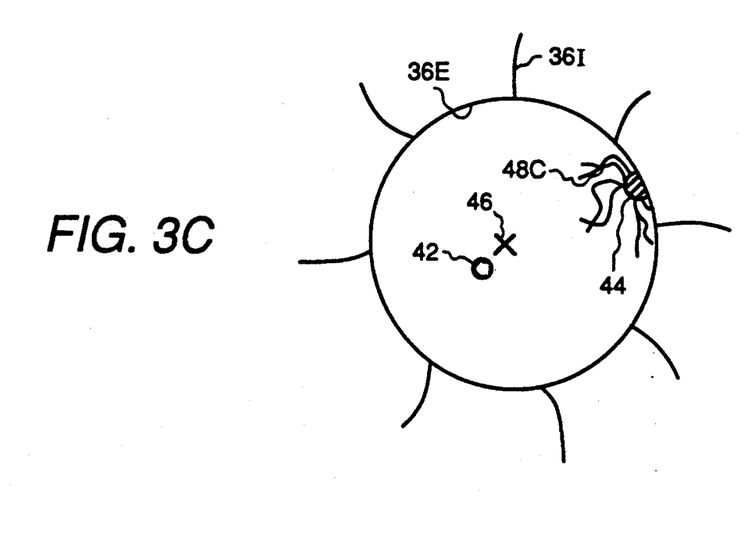

The above discussion of eye alignment information will be more readily understood by reference to FIGS. 3A, 3B, and 3C which show images corresponding to the operation of the present invention. In particular, FIG. 3A shows an iris image 36I having an edge 36E which defines the outside boundaries of the pupil (not separately labeled in these figures). For ease of illustration, the image 36I of the figures is simplified and does not include the large number of irregularities which would be disposed at the image of iris edge 36E. Within the closed loop of edge 36E is the image of the retinal portion corresponding to retinal portion 40 of FIG. 2. In particular, and as shown in FIGS. 3A, 3B, and 3C, this retinal image part of the combined iris portion/retinal portion image includes the fovea 42 and the optical disc 44, both of which are disposed at the retina of the subject's eye.

Although various axes or lines might be used within a subject's eye for defining the alignment of the eye, the discussion which follows makes reference to the pupillary axis, which may be defined as a line between the centroid 46 of the pupil (area within edge 36E in the image figures) and the fovea 42 (more specifically, the center of the foveola). In FIGS. 3A, 3B and 3C, the centroid of the pupil is shown as an "X" 46.

In the view of FIG. 3A, the dextral eye shown therein with the centroid 46 of the pupil disposed at about the mid point between the fovea 42 and the center of optical disc 44. Since the fovea and disc are separated by about 15° in the vision field, the pupillary axis between the centroid and the fovea 42 (more specifically, the center of the foveola, not separately shown) is directed about 7.5° to the right of the alignment instrument axis. The alignment instrument axis ( not separately shown in these figures) has an axis normal to the plane of view of FIGS. 3A, 3B, and 3C. This instrument axis will be considered to extend through the centroid 46 in order to clarify the discussion which follows. Relative positioning between the subject's eye and the eye alignment imaging system or other techniques may be used to provide that the alignment instrument axis extends through the centroid, although it is not essential that a uniquely defined alignment instrument axis extend through the centroid 46. Instead, one might simply define an instrument point of view axis corresponding to the direction of "view" of the instrument and which passes through the centroid 46.

Although the pupillary axis would be directed about 7.5° to the right of the alignment instrument axis (or alignment point of view axis) in the position of FIG. 3A, one can say that the eye is looking about 7.5° to the right of the instrument axis only to the extent that one is certain that the subject's visual axis necessarily extends between the centroid 46 and the fovea 42 (more specifically, center of foveola). For certain purposes, it may be reasonable or necessary to assume that the visual axis of the subject's eye is the same as the pupillary axis. However, the use of the present method does not require that this assumption be made.

In the view of FIG. 3B, the eye orientation has changed so that the pupillary axis is now only a few degrees to the right of the instrument axis. If the fovea 42 were moved slightly to the left in the view of FIG. 3B such that it was centered beneath the centroid 46, then the pupillary axis would be directly in line with the alignment instrument axis (or instrument point of view axis).

In the view of FIG. 3C, the eye has rotated about an axis extending through centroid 46, but the separation between centroid 46 and fovea 42 (i.e., the separation distance as viewed) has remained constant. As shown in the views of FIGS. 3A, 3B, and 3C, the optical disc 44 may have a number of visible fine blood vessels 48 extending near it. The vessels may include crossing points 48C (only one shown for simplicity). By noting that the crossing point 48C has moved counter-clockwise about 30° between the positions of FIGS. 3B and 3C, this indicates that the eye has rotated about 30° counter-clockwise. The centroid 46 may be used as the origin for defining angles of rotation.

The alignment of the eye can thus be established by knowing the relationship between the centroid 46 and the fovea 42. This relationship can establish the angle between the pupillary axis and the instrument axis. However, if the fovea 42 and centroid 46 are both in line with the instrument axis, the position of an additional point must be used in order to determine uniquely or establish alignment of the eye provided that we use the term "alignment" to include rotation about the pupillary axis. Accordingly, use of the image of the optical disc 44 and, especially, the crossings of visible fine blood vessels such as crossing 44C will allow us to uniquely establish the alignment of the eye.

The image of the retina portion as appearing within the iris edge 36E would usually appear as a dark hole in a bright surrounding image because the reflectivity of the iris is much greater than that of the retina in most cases. The substantial detail within the darker retinal image, especially the visible fine blood vessels near the optical disc are quite suitable for computer vision processing. For example, processing can be used to locate and indicate the pupil centroid 46. Various known pattern recognition techniques may be used to compare retinal detail to a reference image of the same eye.

The imaging system 12 used for eye alignment must meet relatively demanding performance requirements to accomplish its full purpose. The eye alignment information must be obtained and indicated in a time that is short compared to the time during which the eye normally changes its alignment significantly. A typical acceptable time is believed to be about 30 to 50 milliseconds. Within a fraction of this time, the imaging system 12 must form an image with sufficient resolution and depth of focus to provide accurate measurement of the pupil centroid and the retinal detail. Typically, the relatively low reflectivity of the retina means that it must be illuminated artificially to satisfy these requirements, but injurious light levels must be avoided. Further, it is best to avoid uncomfortable light levels because eye responses such as accommodation, aversion or blinking may result and may invalidate a diagnostic measurement. The imaging system should also provide frequent images in order to follow eye motion to guide the approach to proper alignment.

By using the general principles of operation of the scanning laser ophthalmoscope (SLO) co-invented by one of the present inventors and described in more detail in the incorporated by reference U.S. Pat. No. 4,213,678, one can provide an imaging system which will meet the criteria specified above. The SLO has two major advantages for providing alignment information based upon the showing of a dual iris image and retinal image. In particular, the SLO provides retinal images at TV rates with relatively low levels of retinal illumination. Further, the SLO, as modified for the present purposes, may provide high resolution with the large depth of focus required to image both the pupil and the retina.

Figure 4:
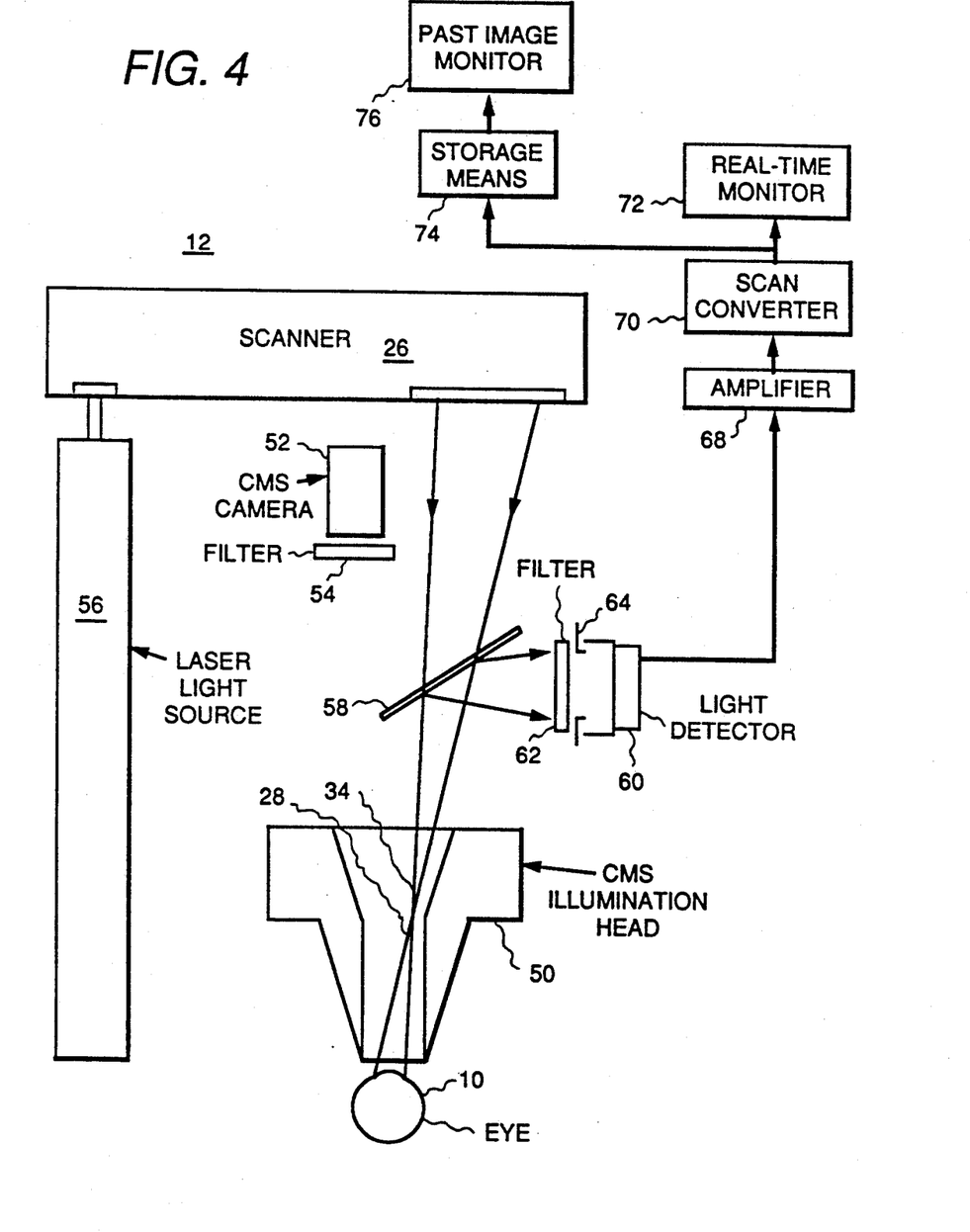
FIG. 4 shows an arrangement wherein the present eye alignment system is operating in conjunction with a known instrument which provides measurements of a cornea of the subject's eye.

FIG. 4 shows the eye alignment imaging system 12 in position for measuring a subject's eye 10, while the eye 10 is, at the same time subject to measurement by a Computer Modeling System (CMS) keratograph having an illumination head 50 and a camera 42. The illumination head 50 and the camera 52 are part of the CMS manufactured by Computed Anatomy, Inc. and designed to provide topographic measurements of a cornea. The CMS head 50 and camera 52 are simply shown in FIG. 4 to illustrate how the present invention may be used in combination with a particular known diagnostic instrument. Additionally, the head 50 and camera 52 are included in FIG. 4 to show a specific manner in which the present imaging system 12 may be used without interference between it and another eye diagnostic instrument. Specifically, the illumination head 50 may use red light and a filter 54 may only allow red light to pass through to the camera 52. In that fashion, the camera 52 will avoid errors which might otherwise be caused by light from the imaging system 12 since the imaging system 12 may use green light from laser source 56.

The green light from laser light source 56 is supplied to a scanner 26 which may scan the beam 28 in a pattern in order to image a retinal portion and an iris portion of the eye 10 as discussed in detail previously. Numerous scanning patterns could be used, but the preferred scanning pattern resembles a conventional interlaced television scanning pattern except that image scanning is continued during the backward sweep, this pattern being discussed in more detail in the incorporated by reference Pomerantzeff patent. The scanner 26 may include various optical elements as will be discussed in detail below. The light from the scanner 26 will pass through the beam splitter 58 on its way to the eye 10. The beam splitter 58 is preferably a polarizing beam splitter. Since the scanner 26 may supply polarized light (by use of a polarized laser 56) and the polarized light is about 98% transmitted through the polarizing beam splitter 58, most of the beam energy from scanner 26 will pass through to the eye 10. Additionally, the reflections from the cornea and lens of the eye 10, which are interfering signals for present purposes, will generally still be polarized such that these reflections will pass through the polarizing beam splitter 58 and will not be directed towards a light detector 60. However, unlike the reflections from the cornea and lens, the scatter returning from the iris and retina are substantially depolarized such that about 50% of the light returning from the surface of interest will be deflected towards the light detector 60. Thus, use of a polarizing laser 56 and a polarized beam splitter 58 allows one to substantially increase the strength of light returning from the surfaces of interest relative to reflections from surfaces which are not of interest for alignment purposes. The reflected light supplied to light detector 60 goes through filter 62 which would be a green filter corresponding to the green light from laser 56. The filter 62 will minimize the response of the light detector 60 to reflections from the red light used by the illumination head 50.

In addition to having the scan crossing point 34 disposed in front of the eye as shown, note that the system does not include any optical elements between that crossing point 34 and the eye 10. Among other modifications to the SLO disclosed by the Pomerantzeff incorporated by reference patent, the diameter of beam 28 would generally be significantly smaller than the diameter used for high resolution at the retina when the SLO is used as a fundus camera in accord with the Pomerantzeff patent. By use of a smaller beam than in the fundus camera application of the SLO, one can get a good focus on the pupil, while at the same time having a sufficient depth of focus that the retina features can be used for alignment purposes. It should briefly be noted that the SLO fundus camera as described in the incorporated by reference Pomerantzeff patent uses a stop 88 in FIG. 1 of that patent having an aperture therein which corresponds to the size of the pupil, thereby preventing the detector from detecting light reflected from the iris. Although the present system 12 may include a stop 64, the stop will have an aperture which is sufficiently wide to allow light from the iris to pass there through. In other words, the light detector 60 will be able to receive reflected light from the iris as well as the retina. The stop 64 may avoid reflections or stray light from outside the area upon which the light beam 28 is applied.

The light detector 60 is connected to an amplifier 68 which provides an output to a scan converter 70. The scan converter 70 in turn supplies an output to a real-time monitor 72. Additionally, the scan converter 70 might be connected to a print-out device (not shown). Generally, the operation of the amplifier 68, scan converter 70, and monitor 72 will be the same as the corresponding components in FIG. 2 of the Pomerantzeff patent. It should also be noted that, for ease of illustration, the timing and synchronization, scan amplitude and centering, X driver and Y driver blocks have not been shown in FIG. 4, it being readily understood that these may operate in the same manner as shown and discussed relative to FIG. 2 of the Pomerantzeff patent.

As shown in FIG. 4, the arrangement may also include a storage means 74 which may store the image of a particular eye alignment (i.e., a combined iris image and retinal image which reveals eye alignment information). The storage means 74 may be a digital memory or any of various known types. Alternately, one could use a videotape recorder (not shown) to store past alignment data, in which case the video tape recorder might be connected directly to the output of amplifier 68.

Regardless of the type of storage means 74 which is used, it may supply a signal to a past image monitor 76. The monitor 76 will show a previous eye alignment in accord with the digital memory, video tape, or other type of storage means 74. Although FIG. 4 shows two separate monitors 72 and 76, these monitors might simply be separate halves of a cathode ray tube (not separately shown) by use of known splitscreen techniques. In that case, one half of the screen would show the past combined iris/retinal image, whereas the other half of the screen would show the real-time combined iris/retinal image. The two separate monitors 72 and 76 may collectively be considered as a monitor means.

By use of the storage means 74, one can use the system 12 to determine that the eye 10 is back into a previous orientation. For example, the eye 10 may be in a relatively arbitrary position when the CMS keratograph is first used. When the keratograph is used, one would also use the imaging system 12 to provide a combined iris/retinal image which would be stored within the storage means 74. A doctor or other person may then perform some therapeutic procedure upon the eye 10. In order to determine what effect, if any, the therapeutic procedure has had upon the topography of the cornea, one would like to remeasure the cornea. However, in order to have meaningful data, the eye 10 must be oriented the same way it was when the cornea measurements were first made.

Ensuring that the post-therapeutic cornea measurements are made with the eye in the same orientation as the pre-therapeutic measurements, one would first position the eye 10 relative to the imaging system 12 to allow it to image the eye. The imaging system 12 would then provide an iris image of the iris portion of the subject's eye and a retinal image of a retinal portion of the eye. This post-therapeutic combined image is then used to determine objective eye alignment. More specifically, the doctor or other medical professional could move the subject's head, or, more directly, his eye until the real-time monitor 72 shows a combined image which is substantially identical to the combined image of the pre-therapeutic combined image which may be on display in the past image monitor 76. In order to return the eye 10 to its same alignment as in the past-therapeutic combined image, the person manipulating the eye would ensure that the relative positions of the pupil centroid 46, fovea 42, and optical disc 44 (refer back momentarily to FIGS. 3A, 3B, and 3C) are the same as in the pre-therapeutic combined image. To that end, the positioning of the crossings of blood vessels 48C (again referring to FIGS. 3A, 3B, and 3C) and the blood vessels themselves may be especially helpful in establishing that eye alignment is the same for the post-therapeutic measurement as it was for the pre-therapeutic measurement. Indeed, one might use several features of the blood vessels around the optical disc to return to a previous alignment without necessarily specifically considering the position of the fovea.

In addition to using various known computer vision processing techniques to automatically supply the centroid 46 (FIGS. 3A, 3B, and 3C), one could alternately simply insert the centroid in the image by the operator locating the centroid and inserting it using known technology to insert points or marks on an image.

Upon the past image monitor 76 and the real-time monitor 72 showing that the post-therapeutic eye alignment is the same as the pre-therapeutic eye alignment, one may then turn on the CMS keratograph to provide the cornea measurements. Since the alignment of the eye 10 is the same as it was when the original cornea measurements were made, differences between the cornea measurements before and after the therapeutic procedure can reasonably be said to result from the therapeutic procedure.

As an alternative to having the operator bring the eye 10 into the same alignment for the post-therapeutic measurement as the alignment in the pre-therapeutic measurement, the past combined iris/retinal image may be compared to the real-time combined image and the difference in orientation could be calculated. In that case, the cornea measurements may be made in a post-therapeutic alignment which is different than the pre-therapeutic alignment, but computer software could be used to provide a transformation to convert the post-therapeutic cornea values into corresponding pre-therapeutic values. To take a simple example, if the pre-therapeutic measurement was made with the pupillary axis in line with the instrument axis, and the eye alignment imaging system 12 shows that the post-therapeutic cornea measurements are being made with the pupillary axis still in line with the instrument axis, but with the eye rotated 30° counter-clockwise about the pupillary axis, the post-therapeutic cornea measurements would be transformed by, in effect, rotating the cornea measurements 30° counter-clockwise about the pupillary axis.

In addition to allowing one to determine eye alignment information by comparison of before and after combined iris/retinal images, a single combined iris/retinal image might be used to determine objective eye alignment in the same fashion as discussed above during the initial explanation of FIG. 3A. In other words, the relative positioning of the fovea 42, optical disc 44 and centroid 46 in FIG. 3A was indicative of the pupillary axis being directed about 7.5° to the left of the alignment instrument axis. Depending upon the degree of accuracy which is required in a particular application, one might assume that the pupillary axis corresponds to the visual axis such that information about the direction of the pupillary axis could be used to infer what the subject (such as a test animal) was viewing. Since the visual axis does not pass through the centroid of the pupil for all subjects, this assumption that the pupillary axis and visual axis coincide would be an inappropriate assumption under other circumstances.

Upon determining the eye alignment by the relationship between the pupillary axis and the instrument axis (and preferably also including some indication about the rotation of the eye), one could continue to track this eye alignment data with the alignment imaging system 12 of the present invention during a therapeutic procedure upon the eye 10. Alternately, one could obtain this alignment data and, in effect, transfer the alignment data to an eye tracker. The eye tracker is a known instrument which is simpler than the present invention, but normally yields incomplete or inaccurate alignment data. By using one of several known types of eye trackers to which the alignment data from system 12 has been transferred, the system 12 may be removed from its position whereas it images eye 10 such that the system 12 will be out of the way of any therapeutic instruments which might be used on the person's eye. The eye tracker will provide information based upon a starting point supplied by the system 12.

Figure 5:
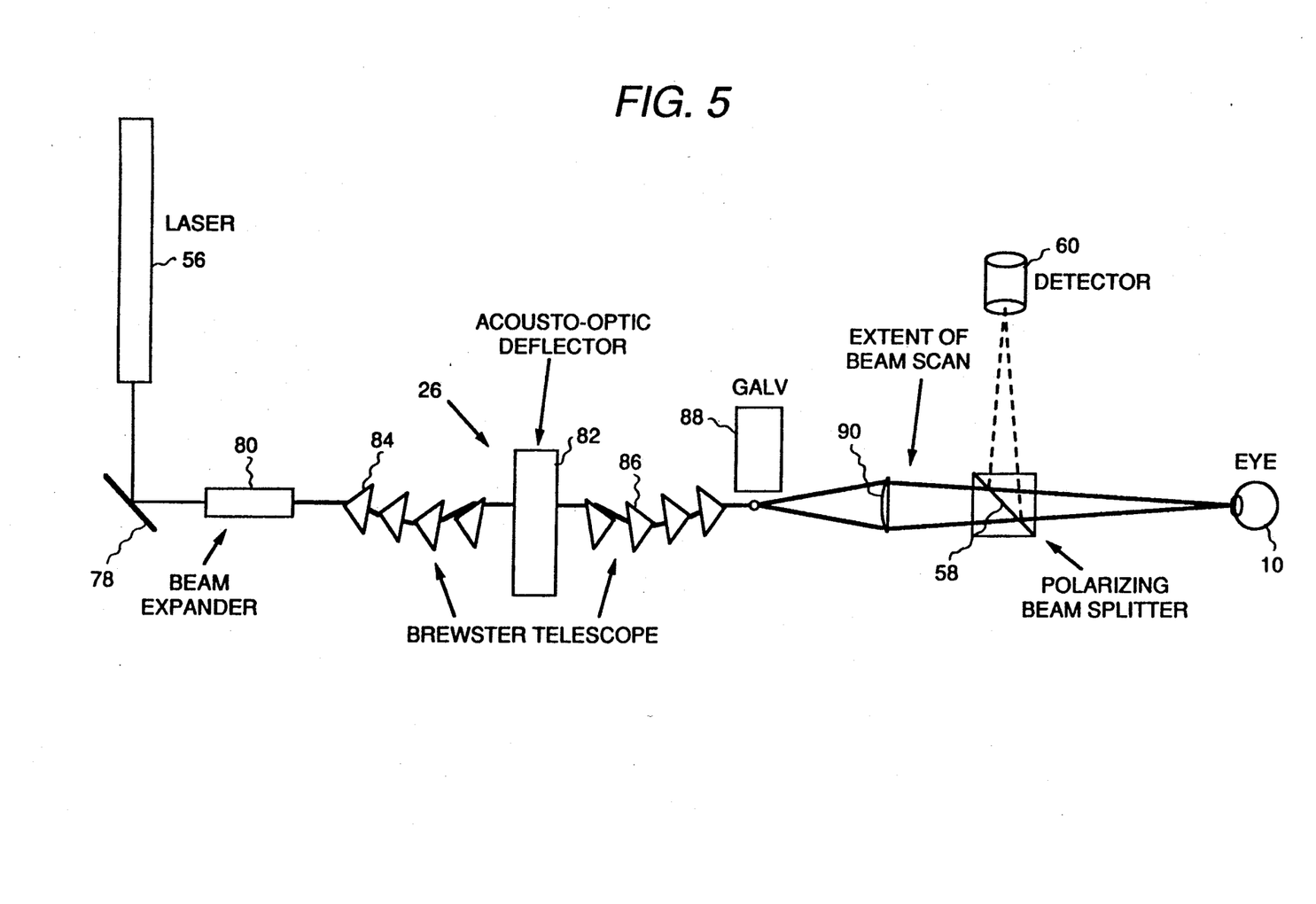
FIG. 5 shows a detailed view of an arrangement which may be used to provide the scanning.

The scanner 26 of FIG. 4 may be constructed in any of various generally known ways to provide the desired scan pattern as discussed above. However, with reference now to FIG. 5, an especially advantageous manner of constructing the scanner 26 will be discussed. The laser light source 56 supplies light to a reflector 78 which reflects the light to a beam expander 80. An acousto-optic deflector 82 may be used to provide TV rate deflection without moving parts or excessive sound. However, the acousto-optic deflector has a large aperture. As the deflector 82 is a diffraction limited device, the number of resolvable positions is proportional to the aperture in the direction of scan. In order to supply a sufficiently large number of resolvable positions, acousto-optic deflectors have large apertures only in the necessary direction. Accordingly, they require a light beam which is much wider than it is high. Although the necessary beam may be provided with cylindrical mirrors and off-axis parabaloids (not shown) or various other anamorphic schemes, the arrangement of FIG. 5 uses a Brewster telescope having prism chains 84 and 86 which are relatively easy to align and more compact than various other anamorphic schemes. The portion 84 of the Brewster telescope in front of the acousto-optic deflector 82 increases one dimension of the beam from expander 80 by four times, whereas the portion 86 of the Brewster telescope after the deflector 82 returns the beam to the same dimensions as it had when entering the first part of the Brewster telescope. Portion 86 of the Brewster telescope also multiplies the scan angle by four. A moving-mirror galvanometer 88 is used to provide vertical deflection, the mirror being shown just above its actual working position for ease of illustration. The light from the reflector 88 would go to a relay lens 90 and on to the polarizing beam splitter 58. (Although the relay lens 90 was not shown in FIG. 4, such a lens would preferably be used between the scanner 26 and polarizing beam splitter 58 of FIG. 4.)

Although various specific constructions have been included herein, it is to be understood that these are for illustrative purposes only. Various modifications and adaptations will be apparent to those of skill in the art.

Accordingly, the scope of the present invention should be determined by reference to the claims appended hereto.

What is claimed is:

1. A method of determining objective eye alignment comprising the steps of:
   positioning a subject's eye relative to an imaging system to allow imaging of the subject's eye;
   applying a beam to the subject's eye;
   using the imaging system to detect a portion of the beam returned after striking the subject's eye and to generate, based on the detected portion of the beam, an iris image of an iris portion of the subject's eye and a retinal image of a retinal portion of the subject's eye; and
   observing positions of said iris image and said retinal image to determine objective eye alignment.

2. The method of claim 1 wherein the imaging system obtains the iris image and the retinal image within a time no greater than 50 milliseconds.

3. The method of claim 2 further comprising simultaneously displaying the iris image and the retinal image on a first monitor of the imaging system.

4. The method of claim 1 wherein the eye alignment is determined by comparing the iris image and the retinal image with a stored image of an iris portion and a retinal portion corresponding to eye alignment at a previous time.

5. The method of claim 4 wherein the eye alignment is determined by finding an eye position at which the iris image and the retinal image are substantially identical to the stored image.

6. The method of claim 1 wherein the eye alignment is determined by finding a relationship between an instrument axis of the imaging system and an axis of the patient's eye.

7. The method of claim 6 wherein the axis of the subject's eye is a pupillary axis.

8. The method of claim 1 further comprising the step of simultaneously displaying the iris image and the retinal image, and wherein the imaging system develops the iris image and the retinal image by scanning the beam across the eye and detecting scatter from the application of the beam to the eye.

9. The method of claim 8 wherein the beam is a light beam.

10. A method of determining objective eye alignment comprising the steps of:
    scanning a light beam from an imaging system across a subject's eye such that the light beam strikes an iris portion adjacent a pupil and strikes a retinal portion;
    detecting, by operation of the imaging system, scattered light from the application of the light beam to the iris portion and the retinal portion;
    generating nearly simultaneous views of the iris portion and the retinal portion by operation of the imaging system; and
    using said nearly simultaneous views to determine objective eye alignment.

11. The method of claim 10 wherein the light beam is scanned between extremes of scan which cross in front of the subject's eye.

12. The method of claim 11 wherein said extremes of scan cross at least 3 centimeters in front of the subject's eye.

13. The method of claim 10 wherein the light beam has a diameter of no more than 1 millimeter.

14. The method of claim 10 wherein the eye alignment is determined by comparing a real-time image to a stored image representative of eye alignment at a previous time.

15. The method of claim 14 wherein the eye alignment is determined by finding an eye position at which the real-time image is substantially identical to the stored image.

16. The method of claim 10 wherein the eye alignment is determined by finding a relationship between an instrument axis of the imaging system and an axis of the subject's eye.

17. The method of claim 16 wherein the axis of the subject's eye is a pupillary axis.

18. A system for measuring objective eye alignment comprising:
   a scanner for scanning a beam across a subject's eye such that the beam strikes an iris portion adjacent a pupil and strikes a retinal portion;
   a detector for detecting scatter from the application of the beam to the iris portion and the retinal portion;
   a stop having an aperture through which scatter from the application of the beam to the iris portion and the retinal portion passes on its way to said detector; and
   a first monitor operatively connected to said detector for showing simultaneous views of the iris portion and the retinal portion based upon the scatter detected by the detector, the simultaneous views providing objective eye alignment information.

19. The system of claim 18 wherein said scanner scans a light beam.

20. The system of claim 18 wherein said scanner scans the beam between extremes of scan which cross in front of the subject's eye.

21. A system for measuring objective eye alignment comprising:
   a scanner for scanning a beam across a subject's eye such that the beam strikes an iris portion adjacent a pupil and strikes a retinal portion;
   a detector for detecting scatter from the application of the beam to the iris portion and the retinal portion;
   a first monitor operatively connected to said detector for showing simultaneous views of the iris portion and the retinal portion based upon the scatter detected by the detector, the simultaneous views providing objective eye alignment information; and a second monitor and storage means to supply the second monitor with a stored image of the iris portion and the retinal portion at a previous time.

22. A system for measuring objective eye alignment comprising:
   a scanner for scanning a beam across a subject's eye such that the beam strikes an iris portion adjacent a pupil and strikes a retinal portion;
   a detector for detecting scatter from the application of the beam to the iris portion and the retinal portion;
   monitor means operatively connected to said detector for showing simultaneous views of the iris portion and the retinal portion based upon the scatter detected by the detector, the simultaneous views providing objective eye alignment information; and
   storage means connected to the monitor means for supplying the monitor means with a stored image of the iris portion and the retinal portion at a previous time.

* * * * *